United States Patent [19]

DeCaprio

[11] Patent Number: 4,682,606

[45] Date of Patent: Jul. 28, 1987

[54] LOCALIZING BIOPSY APPARATUS

[76] Inventor: Vincent H. DeCaprio, 6 Payne Rd., Elmsford, N.Y. 10523

[21] Appl. No.: 825,546

[22] Filed: Feb. 3, 1986

[51] Int. Cl.⁴ .............................................. A61B 10/00
[52] U.S. Cl. ..................................................... 128/754
[58] Field of Search ........... 128/303.1, 303.14, 303.17, 128/751, 754, 303.15, 303.16, 752, 753

[56] References Cited

U.S. PATENT DOCUMENTS

| | | | |
|---|---|---|---|
| 1,867,624 | 7/1932 | Hoffman | 128/754 |
| 2,031,682 | 2/1936 | Wappler et al. | 128/303.15 |
| 2,919,692 | 1/1960 | Ackermann | 128/754 |
| 3,147,749 | 9/1964 | Marsh | 128/751 |
| 3,628,522 | 12/1971 | Kato | 128/751 |
| 3,943,916 | 3/1976 | Vadas | 128/751 |
| 4,011,872 | 3/1977 | Komiya | 128/303.14 |
| 4,200,111 | 4/1980 | Harris | 128/751 |
| 4,314,565 | 2/1982 | Lee | 128/754 |

FOREIGN PATENT DOCUMENTS

| | | | |
|---|---|---|---|
| 2355521 | 1/1978 | France | 128/303.17 |
| 2479680 | 10/1981 | France | 128/754 |
| 401360 | 2/1974 | U.S.S.R. | 128/754 |
| 0854366 | 8/1981 | U.S.S.R. | 128/303.14 |
| 8503214 | 8/1985 | U.S.S.R. | 128/303.14 |

OTHER PUBLICATIONS

"New Biopsy Instruments", Aksenova, Biomed. Eng., 1980.

Primary Examiner—Kyle L. Howell
Assistant Examiner—Max F. Hindenburg
Attorney, Agent, or Firm—Lilling & Greenspan

[57] ABSTRACT

A method and apparatus for localizing and excising masses which are not palpable in human tissue. A surgical needle is inserted into a located mass and encircled by a cork screw device which is twisted around the mass until the tip of the worm is just beyond the furthest side of the mass from the operator. Subsequently, the handle of the cork screw device is removed and replaced with a guiding extension rod which is used to direct the surgeon as to the depth of the mass in the patient's tissue. A cutting instrument having an inner cylinder and a hollow outer barrel attached to cutting jaws with knife edges is inserted over one end of the extension rod, with the jaws in an open position, and twisted around the worm of the cork screw into the patient's tissue. The cutting jaws of the instrument are opened by pushing finger flanges away from the surgeon causing the cutting jaws to pivot outwardly into an open position. When positioned, the cutting edges are closed by pulling the finger flanges toward the surgeon whereby the hinges press against one end of the inner cylinder causing the jaws to pivot inwardly, to close the cutting jaws and cut by means of the knife edges through the tissue around the mass. At the completion of the excision of the mass, the cylinder is removed with the cutting jaws in a closed position along with the biopsy mass, the cork screw worm and the extension rod.

10 Claims, 17 Drawing Figures

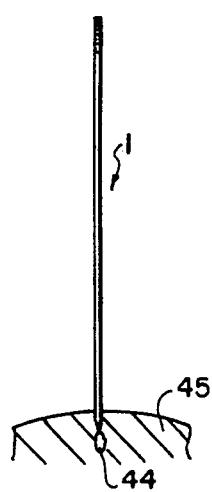
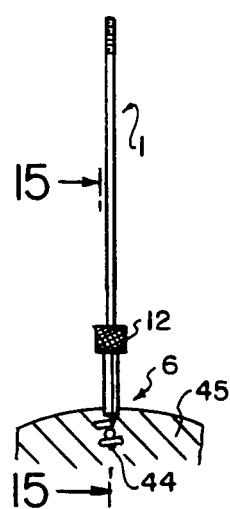
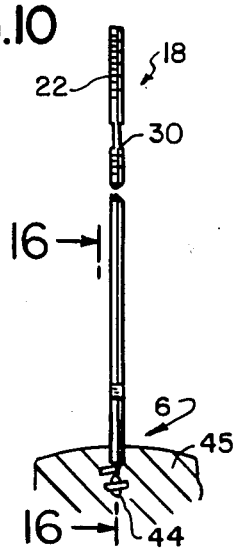
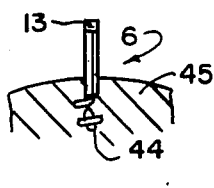
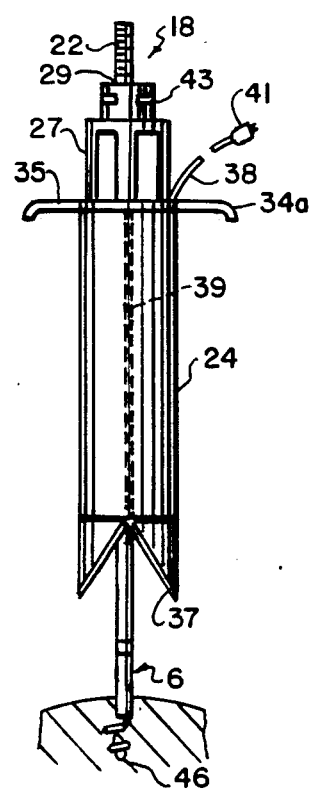
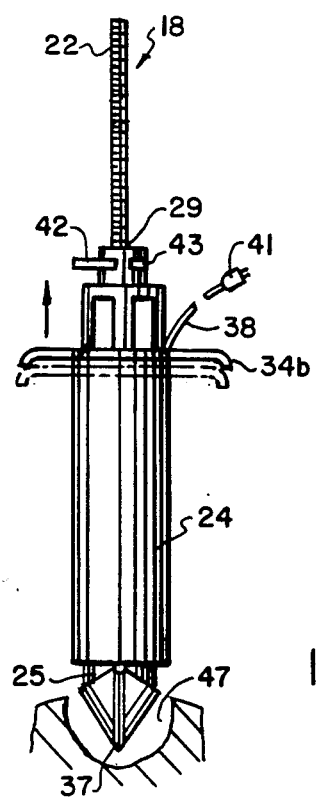
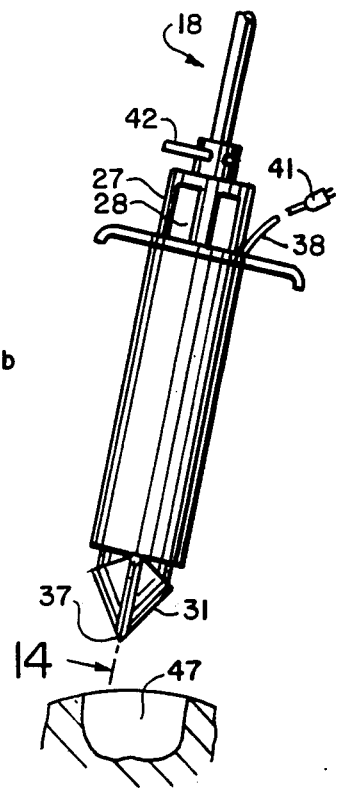

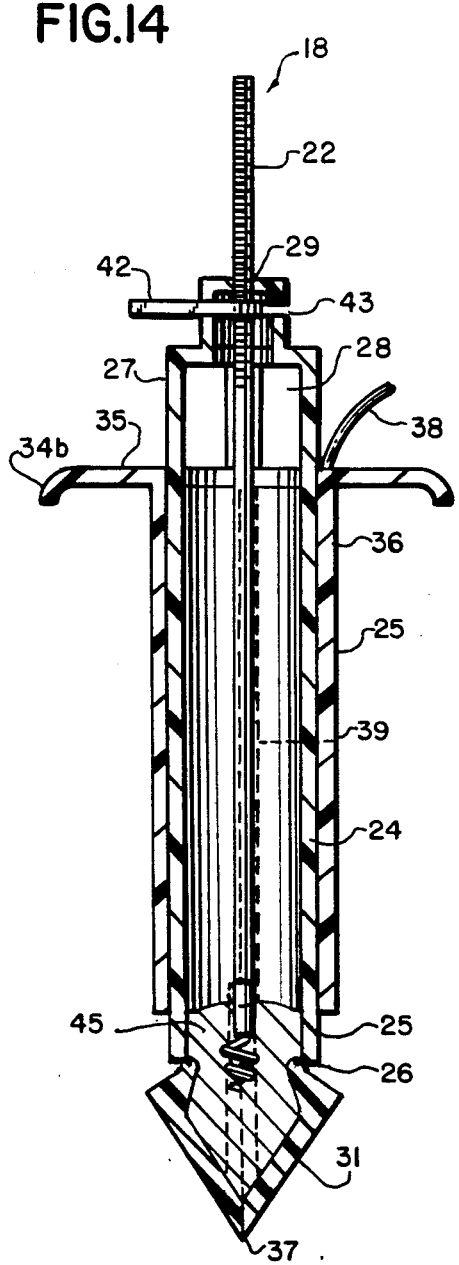
FIG.14
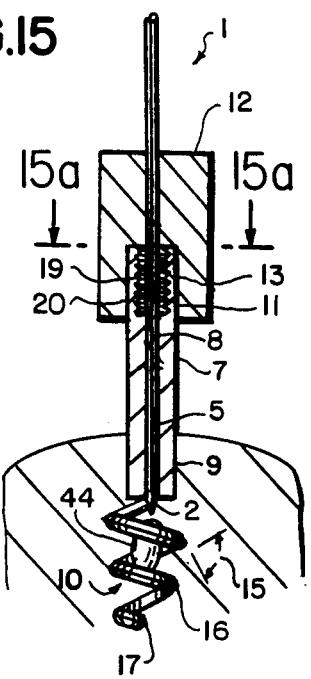
FIG.15
FIG.15a
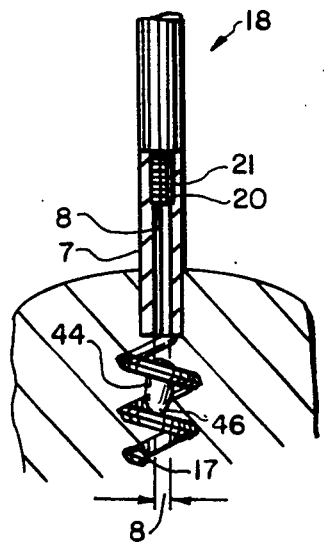
FIG.16

LOCALIZING BIOPSY APPARATUS

BACKGROUND OF THE INVENTION

Biopsy masses or tumors in human tissue which are palpable by a surgeon can be localized by touch to be removed during surgery. Many biopsy masses, however, are too small to be palpable or are located in fatty tissue which interferes with the surgeon's perception of the exact location of the tumor or mass. This is particularly true with small breast masses, which, prior to the subject invention, have been located mostly by imprecise methods requiring more expenditure of time to entirely remove the mass.

Moreover, prior art methods of removing masses which are unpalpable require the use of several different instruments during the operation causing undue manipulation of the surrounding tissue and exposing the tissue prior to the removal of the mass.

Thus, an object of this invention is to provide a method and apparatus for precisely locating an unpalpable tumor or abnormal mass in the earliest possible stage of detection without causing undue mutilation of the surrounding healthy tissue, and ensuring the complete removal of the targeted mass. The subject invention creates a single channel through the surrounding tissue to the targeted mass avoiding a multiple use of surgical instruments and unneccessary exposure of the surrounding tissue.

SUMMARY OF THE INVENTION

To localize and excise a mass, a radiologist and a surgeon working in cooperation proceed by the following method. The radiologist localizes the mass by means of a radiogram and inserts a surgical needle into it. A cork screw device having a hollow central shaft is then inserted over the positioned surgical needle and screwed into the patient's tissue until the tip of the worm element of the cork screw device is just beyond the side of the mass farthest from the radiologist. At this point in the procedure, the radiologist applies a simple dressing over the exposed end of the cork screw device and the patient is transported to the operating room.

The surgeon proceeds with the operation by twisting a cutting instrument to a pre-determined depth around the cork screw device. Knife edges on the cutting jaws of the cutting instrument are in an open position prior to the insertion of the instrument by the surgeon into the patient's tissue. Once the cutting edges are positioned at a level below the side of the mass farthest from the surgeon, the surgeon closes the cutting jaws cutting through the tissue around the mass and at the same time applying an electrical current to the knife edges to aid in cutting and cauterizing the incision area. Once the mass has been excised from the healthy surrounding tissue, the surgeon removes the cutting instrument encompassing the targeted mass and the cork screw device. The resulting wound in the tissue where the mass was removed can be inspected by the surgeon for excessive bleeding and subsequently controlled.

The surgical needle used to localize the mass has a graduated scale on one end which is used to determine the depth of the mass in the tissue. The outer diameter of the needle is slightly less than the inside diameter of the hollow central shaft of the cork screw device which accommodates it. The radiologist twists the worm of the cork screw device into the patient's tissue to the exact depth by using the graduated scale on the surgical needle. Once positioned, the surgical needle and the handle of the cork screw device are removed prior to dressing and transporting the patient. In the operating room, a surgeon threads a guiding extension rod to one end of the cork screw device extending from the patient's tissue to guide the cutting instrument to the exact location of the mass.

Cutting jaws having knife edges are pivotally attached to the outer hollow barrel of the cutting instrument and attached by means of a hinge to an inner wall of an inside cylinder accommodated inside the hollow outer barrel. Finger flanges on the opposite end of the outer barrel from the cutting jaws are pulled toward the surgeon which causes the outer barrel to slide toward the operator closing the cutting jaws together. The cutting jaws are opened by reversing the above procedure.

An electrical wire embedded in a channel in the outer cylinder of the cutting instrument supplies an electrical current to the knife edges of the cutting instrument to aid in cauterizing and cutting the tissue. Once the cutting edges are positioned at a level below the side of the mass farthest from the surgeon, the surgeon closes the cutting jaws cutting through the tissue around the mass and at the same time the surgeon applies an electrical current to the knife edges to aid in cutting and cauterizing the incision area. Once the mass has been excised from the healthy surrounding tissue, the surgeon removes the cutting instrument encompassing the localized mass and the cork screw device. The resulting wound in the tissue where the mass was removed can be inspected by the surgeon for excessive bleeding and subsequently controlled.

BRIEF DESCRIPTION OF THE DRAWINGS

FIG. 7 illustrates the surgical needle prior to insertion in the mass in situ.

FIG. 8 is a sequential view of the needle shown in FIG. 7, surrounded by the cork screw device.

FIG. 9 is a sequential view of the cork screw device shown in FIG. 8 with the handle removed.

FIG. 10 is a sequential view of the cork screw device shown in FIG. 9 with the guiding extension rod connected to the cork screw device.

FIG. 11 is a sequential view of the guiding extension rod and the cork screw device shown in FIG. 10 surrounded by the cutting instrument.

FIG. 12 is a sequential view of the cutting instrument illustrating the cutting jaws in a closed position following the cutting step.

FIG. 13 is a sequential view of the cutting instrument shown in FIG. 12 illustrating the removal of the instrument from a patient's tissue.

FIG. 14 is a cross-sectional view of a cutting instrument taken along lines 14—14 of FIG. 13. FIG. 15 is a cross-sectional view taken along lines 15—15 of FIG. 8.

FIG. 15a is a cross-sectional view taken along lines 15a—15a of FIG. 15.

FIG. 16 is a cross-sectional view taken along lines 16—16 of FIG. 10.

DETAILED DESCRIPTION OF THE INVENTION

Referring to FIGS. 1-4, the inventive apparatus consists of a surgical needle 1, a cork screw device 6, a guiding extension rod 18, and a cutting instrument 23.

Figure 2:
FIG. 2 is a side view of the surgical needle.

The surgical needle 1 preferably has a pointed tip end 2 with a graduated scale 3 at the other end 4 as illustrated in FIG. 2. Preferably, the surgical needle 1 is manufactured of an inflexible material such as metal or plastic with a bonded tip end 2, which can be sterilized and would not bend or break during usage, however, any suitable material known in the art which can be sterilized can be used.

The outer diameter 5 of the surgical needle 1 determines an inside diameter 8 of a shaft 7 of the cork screw device 6, which accommodates the surgical needle 1. Since most of the masses which are not palpable and are most accessible by the claimed invention are small in diameter, the preferred outside diameter 5 of the surgical needle ranges from 0.5 to 4.5 millimeters. Thus the preferred inside diameter 8 of the cork screw shaft 7 ranges from 1 to 5 millimeters or slightly greater than the outer diameter 5 of the needle 1, so that the needle can easily be accommodated in the hollow shaft 7. However, it should be noted that the inventive apparatus can be used to localize an unpalpable tumor of any size and thus the outer diameter 5 of the surgical needle 1 and the inside diameter 8 of the cork screw shaft 7 may be designed relative to the size of the located tumor as illustrated in FIGS. 15-16.

At one end 9 of the shaft 7 of the cork screw device 6 is a worm element 10 and at the other end 11 of the cork screw device shaft 7 is a removable handle 12. As illustrated in FIGS. 15 and 15a, in the preferred embodiment, the handle 12 is manufactured having a knurled outer surface so that the instrument can be firmly gripped. Moreover, a square-shaped cutaway 13 inside one end of the handle 12 press fits around a square-shaped outer diameter 19 of the end 11 of the shaft 7 of the cork screw device 6 to facilitate easy removal of the handle 12 by pulling it off the shaft 7 of the cork screw device 6.

A pull-off handle 12 as illustrated in FIG. 15 is preferred because the shape allows a surgeon to clamp a hemostat or other instrument to the shaft of the cork screw device 6 during the operating procedure. Further, pulling the handle 12 from the cork screw device 6 prevents dislodging of the cork screw device 6 from the tissue, which frequently occurs with handles which must be removed by unscrewing them. It may be appreciated, however, that the handle 12 may be attached to the cork screw device 6 by any other means known in the art.

Further, in the preferred embodiment, the worm element 10 should be of a rigid material, such as metal, which can be twisted to form a flattened design at each turn 16 of the worm element as illustrated in FIG. 15. This design ensures less resistance as the worm element 10 is twisted into the patient's tissue. To achieve the flattened design, the width of the worm element 10 may be 1 centimeter, and the angle 15 between each turn 16 may be 20-30° as illustrated in FIG. 15. The worm element 10 ends in a sharpened tip end 17 which is used to bore into the patient's tissue, and will facilitate the removal of the complete mass.

To extend the length of the shaft 7 of the cork screw device 6, the handle 12 and surgical needle 1 are removed from the cork screw device 6 and replaced with a guiding extension rod 18 as illustrated in FIGS. 8-10.

Once the handle 12 is removed, the guiding extension rod 18 can be inserted into an opening 20 located inside the square-shaped outer end 11 of the cork screw device to extend the length of the shaft 7 of the cork screw device 6. The diameter of the internal opening 20 contains threads 19 and is wider in diameter than the surgical needle's outer diameter 8 as illustrated in FIGS. 15 and 15a. On one end of the extension rod 18 is a threaded nipple 21 which is used to screw the rod 18 snugly into the threads 19 of the internal opening 20 in the cork screw shaft 7 as illustrated in FIG. 16. Other means known in the art may be used to connect the extension rod 18 into the opening 20. At the other end of the rod 18 is a graduated scale 22 used to indicate the depth of a cutting instrument 23 in the patient's tissue.

Figure 1:
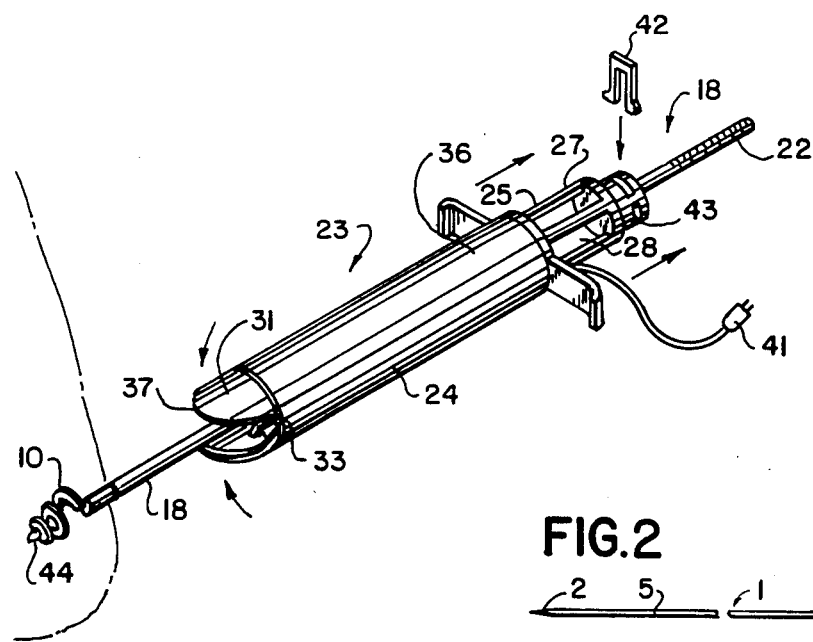
FIG. 1 is a perspective view of the biopsy localizing and excising apparatus.

Once the rod 18 is positioned, the cutting instrument 23 is utilized as shown in FIG. 1. The cutting instrument 23 has an outer barrel 24 which is hollow to accommodate an inner cylinder 25. In the preferred embodiment, the outer barrel 24 is made of a hollow plastic material which prevents tissue or body fluids from discharging through the barrel 24 during the operation of the instrument 23 and the inner cylinder 25 is snugly press fitted into the outer barrel 24. Although the inner cylinder 25 may be molded as either a hollow cylinder or formed by ribs extending from a hinge end 26 to a slot end 27, in the preferred embodiment as shown in FIG. 14, a perforated area 28 is provided at the slot end 27 of a hollow inner cylinder 25 to prevent the build up of fluids during the operation of the instrument 23. Further, a channel 29 is defined by the walls of the inner cylinder 25 to permit the cork screw device 6 and the extension rod 18 to pass through the cutting instrument 23.

Figure 5:
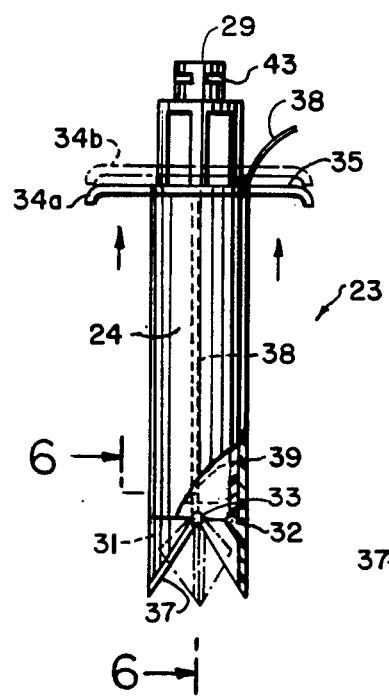
FIG. 5 is a side elevational view in partial cross-section, illustrating the closed position of the cutting instrument in phantom lines.
Figure 3:
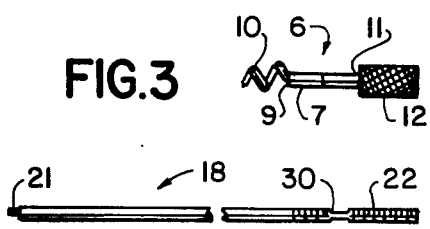
FIG. 3 is a side view of the cork screw device.
Figure 4:
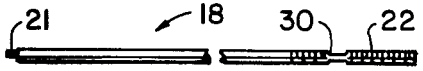
FIG. 4 is a side view of the guiding extension rod.
Figure 6:
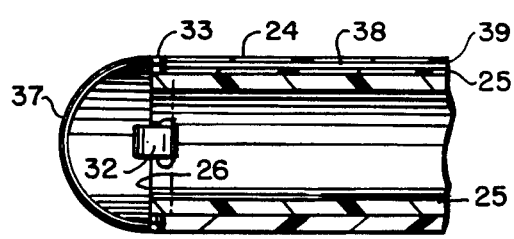
FIG. 6 is a cross-sectional view taken along lines 6—6 of FIG. 5.

A pair of cutting jaws 31 are attached to the inner cylinder 25 by means of a pair of hinges 32 as illustrated in FIGS. 6 and 14. The cutting jaws 31 are preferably shovel-shaped and are designed to pivot about pivot points 33 attaching the jaws 31 to the outer barrel 24 as illustrated in FIGS. 1 and 5. Preferably, the pivot pivot points 33 are diametrically opposed on the outside wall of the outer barrel 24 and the hinges 32 are located halfway between the pivot points 33 and diametrically opposed on the slot end 27 of the inner cylinder 25.

To close the cutting jaws 31, the outer barrel 24 is pulled toward an operator, which in turn moves the hinges 32 against the hinge end 26 of the inner cylinder causing the cutting jaws 31 to pivot inwardly around the pivot points 33 and come together, as is well known in the art. The inner cylinder 25 remains stationary during the manipulation of the cutting jaws 31. To reverse the procedure and move the jaws 31 to an open position 34a, the operator pushes the outer barrel 24 away from him. The open 34a and closed 34b positions of the cutting jaws are illustrated in FIGS. 5 and 14.

Although any means known in the art may be used to facilitate the movement of the barrel 24 by the operator, in the preferred embodiment as illustrated in FIGS. 1, 5 and 14, a set of finger flanges 35 is attached to a second end 36 of the barrel 24. The opened and closed positions 34a, 34b of the cutting instrument 23 are shown in FIG. 5, with the closed position 34b of the cutting jaws 31 and finger flanges 35 shown in phantom lines.

Knife edges 37 outline the periphery of the set of cutting jaws 31. In the preferred embodiment, the cutting jaws 31 are made of plastic and the knife edges 37 are made of a metal material. A smooth cutting edge 37 is preferable to a serrated knife edge for a smoother cut through the tissue. When the cutting jaws 31 are closed, the knife edges 37 cut through the targeted tissue as the jaws 31 pivot about their pivot points 33 to their closed position 34b.

To cauterize the surrounding tissue and to facilitate the cutting of the knife edges 37, an electrical current is provided to them. *As illustrated in FIGS. 5, 6, 11 and 14 an electrical wire 38 is preferably embedded in a channel 39 in the outer barrel 24 of the cutting instrument 23 and traverses the outer barrel 24 ending at one of the pivot points 33 to conduct the electrical current to the knife edges 37. A free end of the electrical wire 38 is attached to a plug 41 which may be plugged into any outlet convenient to the user.

Channel 29 of the inner cylinder 25 of the cutting instrument 23 accommodates the extension rod 18. When the extension rod 18 is positioned in the channel 29, a clip 42 is inserted into a slot 43 around the extension rod 18 at the position of a notch 30 to hold the rod 18 together with the inner cylinder 25. Thus, when the cutting instrument 23 is operated, the extension rod 18 is prevented from moving freely in the channel 29 and the accurate cutting of the instrument 23 is insured. As illustrated in FIGS. 1 and 14, the slot 43 is duplicated on the opposing portion of the end 26 of the inside cylinder 25 so the ends of the clip 42 can spring securely into position and to give the user a choice of clipping the rod 18 from either side of the cutting instrument 23 during its use.

The localization and removal of an abnormal mass 44 by the above described apparatus is accomplished by the following procedure. A radiologist locates the position of a mass 44 in a patient's tissue 45 by means of a radiogram. Once the mass 44 is located, the pointed tip end 2 of the surgical needle 1 is inserted into the mass 44, as shown in FIG. 7. The depth of the mass 44 in the patient's tissue 45 is determined by using the graduated scale 3 on the end 4 of the surgical needle 1.

Subsequently, as illustrated in FIG. 8, the radiologist inserts the worm element 10 of the cork screw device 6 over the end 4 of the surgical needle 1 and twists the device 6 towards the patient's tissue 45 by turning the handle 12 in a circular direction. The tip 17 of the worm element 10 bores into the tissue 45 and encircles the surgical needle tip end 2 and the located mass 44 until the tip 17 is beyond the side 46 of the mass 44 farthest from the radiologist, as illustrated in FIGS. 8 and 15.

Once the worm element 10 is positioned around the located mass 44, the radiologist removes the handle 12 from the cork screw device 6 leaving only a short length of the shaft 7 of the cork screw device 6 extending beyond the tissue 45 of the patient, as illustrated in FIG. 9. At this point, a simple dressing is placed over the end 11 of the cork screw device 6 and the patient can be transported to an as operating room for the remainder of the procedure.

Once in the operating room, as illustrated in FIG. 10, the guiding extension rod 18 is attached to the end 11 of the cork screw device 6 to aid the surgeon in guiding the cutting instrument 23 into its proper position. Extension rods 18 vary in length depending on the length of the cork screw shaft 7 which projects above the level of the patient's tissue. For example, if the mass is located deep under the patient's skin level only a short section of the shaft 7 will extend above the skin requiring that the surgeon use a longer extension rod 18 to guide the cutting instrument 23 into position. The notch 30 in each of the rods 18 would also vary in position along the rod's length.

When the rod 18 is positioned, the surgeon pushes the finger flanges 35 of the cutting instrument 23 away from him causing the cutting jaws 33 to pivot outwardly to an open position 34a and the cutting instrument 23 is inserted around the extension rod 18 as illustrated in FIG. 11. To facilitate the movement of the cutting instrument 23 into the patient's tissue 45, an incision is made on either side of the shaft 7 of the cork screw device 6 in the patient's tissue 45.

The surgeon twists the cutting instrument 23 around the extension rod 18 and cork screw device 6 until the cutting jaws 23 are at a level in the patient's tissue 45 just beyond the tip 17 of the worm element 10. This depth is determined by calculations involving the scale 22 on the extension rod 18. At the determined depth, the cutting instrument 23 is positioned and the extension rod 18 is clipped to the inside cylinder 25 by means of the clip 42 and notch 30. At this point, the surgeon pulls the finger flanges 35 towards him causing the cutting jaws 31 to pivot and move the knife edges 37 towards each other. During this movement, the knife edges 37 cut the tissue surrounding the biopsy mass 44 and encircle the biopsy mass 44 and worm element 10.

At the same time that the jaws 31 are cutting through the tissue 43, the surgeon applies an electrical current through the electrical wire 38 aiding in the cutting process and cauterizing the exposed capillaries in the excised area 47. Once the biopsy mass 44 has been localized and excised, the cutting instrument 23 is removed from the patient's tissue 45 along with the mass 44, cork screw device 6, and extension rod 18. If desired, the excised area 47 may be checked by the surgeon, by inserting a transparent cylinder of any suitable material into the area 47 and observing the tissue 45 for excessive bleeding. At the end of the procedure, the wound is closed and a surgical dressing is applied over the excised area 47 to complete the operation.

I claim:

1. An apparatus for localizing and excising a mass from a patient's tissue comprising:
    a surgical needle having first and second ends, and said first end of said surgical needle being insertable into said mass of said patient's tissue;
    a cork screw means having a hollow central shaft, a worm element attached to a first end of said shaft and a removable handle connected to a second end of said shaft, said cork screw means fitting over said surgical needle and said worm element encircling and localizing said mass when said cork screw means is inserted into said patient's tissue;
    a guiding extension rod having first and second ends, and said first end of said guiding extension rod being connected to said second end of said hollow central shaft of said cork screw means when said removable handle is removed;
    a cutting instrument having an outer barrel and an inner cylinder concentrically accommodated inside said outer barrel, a pair of arcuate cutting jaws being attached to a first end of said outer barrel and a first end of said inner cylinder, said inner cylinder having a channel through which said cork screw means and said guiding extension rod extend, movement of said outer barrel relative to said inner cylinder causing said arcuate cutting jaws to close and to cut said mass from said patient's tissue, and said mass, said guiding extension rod and said cork screw means being removable through said channel of said inner cylinder of said cutting instrument after said mass is cut from said patient's tissue.

2. An apparatus according to claim 1, wherein at least two turns of said worm element of said cork screw means are flattened and separated from each other to encircle said mass.

3. An apparatus according to claim 1, wherein said surgical needle has an outer diameter of a range from 0.5 to 4.5 millimeters and said hollow central shaft of said cork screw device has an inside diameter of a range from one (1) to five (5) millimeters.

4. An apparatus according to claim 1, wherein said barrel of said cutting instrument is hollow and a second end of said cylinder of said cutting instrument is perforated for the discharge of undesired fluid.

5. An apparatus according to claim 4, wherein said barrel and said cylinder are made of a plastic material.

6. An apparatus according to claim 1, wherein said second end of said cylinder has at least one slot; and further comprising a clip inserted into said slot to hold said guiding extension rod stationary with respect to said cylinder when said cutting instrument is activated to excise the mass.

7. An apparatus according to claim 1, wherein said means for manipulating said barrel comprises at least one finger flange attached to a second end of said barrel.

8. An apparatus according to claim 1, wherein said cutting jaws of said cutting instrument are shovel-shaped and made of a plastic material, and cutting edges of said cutting jaws are made of metal.

9. An apparatus according to claim 1, further comprising at least one hinge attaching said cylinder of said cutting instrument to a first end of said cutting jaws and at least two pivot points attaching said cutting jaws to said first end of said barrel, whereby movement of said barrel causes movement of said hinge in the same direction to cause said cutting jaws to pivot about said pivot points.

10. An apparatus according to claim 1, further comprising electrical conducting means connected to an inside wall of said barrel and to the pivot point of said cutting jaws, to deliver electric current to said knife edges of said cutting jaws to cut and cauterize said patient's tissue.

* * * * *